United States Patent [19]

Shier

[11] 4,082,748

[45] Apr. 4, 1978

[54] PROCESS FOR PRODUCTION OF OXAZINE DIONES

[75] Inventor: George D. Shier, Midland, Mich.

[73] Assignee: The Dow Chemical Company, Midland, Mich.

[21] Appl. No.: 718,292

[22] Filed: Aug. 27, 1976

[51] Int. Cl.$^2$ .................. C07D 265/00; C07D 273/00; C07D 295/00
[52] U.S. Cl. ..................................................... 544/98
[58] Field of Search .................................. 260/244 R

[56] References Cited

U.S. PATENT DOCUMENTS 3,799,927  3/1974  Newman ........................... 260/247.1

FOREIGN PATENT DOCUMENTS 434,260  10/1967  Switzerland ........................ 260/244

Primary Examiner—Albert T. Meyers
Assistant Examiner—D. W. Robinson
Attorney, Agent, or Firm—Glwynn R. Baker

[57] ABSTRACT

N-substituted cyclic imides of diacids such as oxydiacetic acid and N-substituted iminodiacetic acid are produced by contacting a hydroxy amide of the formula $HOCH_2CH_2\text{-}A\text{-}CH_2\text{-}CONHR$ with a reduced copper dehydrogenation catalyst at a temperature of about 200°–300° C, A representing —O— or

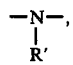

and R and R' being hydrocarbon groups of 1–8 carbon atoms. The reaction is preferably conducted in the presence of hydrogen and the diol corresponding to the hydroxyamide. The process is essentially a means of making oxydiacetic acid or iminodiacetic acid from diethylene glycol or diethanolamine respectively as the original starting material. These dicarboxylic acids are useful chelating agents, particularly for Ca and Mg ions, they are intermediates in chemical syntheses, and they are difunctional monomers for making polyester plastics.

4 Claims, No Drawings

PROCESS FOR PRODUCTION OF OXAZINE DIONES

BACKGROUND OF THE INVENTION

The present invention is a new chemical process for making cyclic dicarboxylic acid imides and thereby the corresponding diacids. More specifically the invention relates to a process for making substituted cyclic imides of oxydiacetic acid and N-substituted iminodiacetic acid by a dehydrogenation process.

It is known that p-dioxanone is formed when the vapors of diethylene glycol are passed over a copper dehydrogenation catalyst such as copper chromite. This process is described by H. R. Guest et al. in U.S. Pat. No. 2,900,395. It is also known that an N-alkyldiethanolamine is dehydrogenated to the N-alkyl-2-morpholinone by an analogous process as described by Schultz et al., U.S. Pat. No. 3,073,822 and by Cenker, U.S. Pat. No. 3,324,123. The present process represents a step beyond these disclosures of the prior art.

SUMMARY OF THE INVENTION

It is now been found that a somewhat similar dehydrogenation and cyclization takes place when a hydroxy substituted amide of the formula

HOCH$_2$CH$_2$-A-CH$_2$CONHR is contacted with a reduced copper dehydrogenation catalyst at a temperature of about 200°-300° C, preferably at 250°-285° C, a cyclic imide of the formula

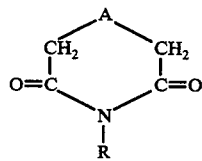

being formed thereby as the only substantial product of the reaction. In the above formulas, A represents —O— or

and R and R' each represent a hydrocarbon group of 1-8 carbon atoms, preferably methyl groups. R and R' can be alkyl such as methyl, ethyl, isopropyl, hexyl, or 2-ethylhexyl, they can represent aromatic groups such as phenyl and tolyl, and they can represent aralkyl groups such as benzyl and phenethyl.

DETAILED DESCRIPTION

The dehydrogenation reaction can be run in either the liquid phase or the vapor phase. In some cases, the size of the R groups makes the liquid phase the only practical mode of operation whereas when R and R' are methyl groups, the vapor phase reaction is preferred. In both liquid and vapor phase operation, the reaction is preferably carried out in the presence of excess hydrogen, for example, about 1.5-10 moles per mole of hydroxy amide feed. In this way, the activity of the catalyst is maintained at a high level for long periods of operation. An inert diluent gas such as nitrogen, argon, or helium may be mixed with the hydrogen in order to moderate catalyst surface temperatures.

Any reduced copper catalyst active in hydrogenation-dehydrogenation reactions is operable in the process, for example, copper metal, copper on a support such as pumice or alumina, or copper promoted by chromium. Copper chromite catalysts are preferred and catalysts having a Cu/Cr weight ratio from 0.8/1 to 4.5/1 have all been used successfully. Prior reduction with hydrogen at about 200° C is necessary to obtain highest activity and the reduction is best carried out using a mixture of hydrogen and nitrogen to avoid unduly high temperature peaks which can cause sintering of the catalyst surface and loss of activity. After prolonged usage, catalyst activity can be restored by an air or air plus nitrogen oxidation at about process temperature followed by reduction with hydrogen as described.

Pressure is not a critical condition in the reaction and the process can be carried out at substantially any subatmospheric or moderate superatmospheric pressure. Operation of the process at or near normal atmospheric pressure is usually preferred.

The hydroxy amide starting material is conveniently prepared by reacting a hydrocarbon primary amine, preferably methylamine, with p-dioxanone (when A in the general formula is oxygen) or with a 4-substituted-2-morpholinone (when A is

Since the amine reaction is rapid and exothermic, it is often convenient to prepare the starting amide in situ by mixing the amine with the dioxanone or morpholinone in the fore part of the reactor.

In view of the fact that the p-dioxanone or morpholinone can be readily prepared by a dehydrogenation reaction similar to the presently claimed process using the same catalyst and reaction conditions, a particularly preferred mode of the present process comprises combining a solution of p-dioxanone in diethylene glycol with methylamine and passing the vaporized reaction mixture with excess hydrogen through the catalyst bed at the process temperature to make the N-methylglycolimide. The presence of the diol in the feed also helps to moderate the reaction and prolong catalyst life. When the desired product is the corresponding N-methyl imide of N-methyliminodiacetic acid, the solution, of course, would be N-methyl-2-morpholinone in N-methyldiethanolamine. In this way, the reaction product is essentially a mixture of the desired imide and the dioxanone or the morpholinone which can be separated by crystallization or distillation and recycled to the process. The starting materials required for the process are thus limited to the amine and the diol, in this instance diethylene glycol or N-methyldiethanolamine, plus the diluent hydrogen. Preferably, the proportion of amine employed is about a molar equivalent or slightly less for example, about 0.9-1 mole, based on the dioxanone or morpholinone in the feed.

As noted above, methylamine is ordinarily the amine of choice to facilitate operation in the vapor phase. In some cases, other amines which produce imides of higher boiling point may improve the efficiency of distillation to separate the reaction product. Amines of higher molecular weight may also necessitate changes in reaction conditions, for example, operation under reduced pressure to maintain vapor phase reaction or a liquid phase process where the liquid feed mixture is trickled through the catalyst bed.

In the same way, when A in the general formula above is

and the original starting diol is a substituted diethanolamine, R' can be an alkyl group higher than methyl such as ethyl, isopropyl, butyl, or octyl, an aralkyl group such as benzyl or phenethyl, or an aromatic group such as phenyl or tolyl. The higher vapor pressure of the resulting intermediates and product may require similar adjustments in process conditions.

It has been found that for the best results in conversion of hydroxyamide and yield of cyclic imide, the space velocity of the liquid feed is maintained in the range of 0.2–5 volumes per volume of catalyst bed per hour. Preferably, the liquid space velocity is held at about 0.5–2.

EXAMPLE 1

The reactor was a vertical 15 mm O. D. Vycor tube with a 6 mm O. D. Vycor thermocouple well running down its center. The reactor was heated by an automatically controlled tube furnace. A mixture of 7.1 g. (5 ml) of 20–40 mesh copper chromite (Girdler G-13 catalyst, Cu:Cr=1.62:1) with an equal volume of 16 mesh silicon carbide formed a bed about 12 mm deep in the reactor tube. The catalyst bed was supported by a short bed of the granular silicon carbide and a bed of about equal depth of the same silicon carbide above the bed of catalyst acted as a preheater. The catalyst was activated at 200° C by passing a mixture of 20 ml/min. $H_2$ and 200 ml/min. $N_2$ through it until the resulting exotherm had moved through the bed. This kind of activation was used for all of the catalysts in the following examples.

A feed mixture of 20.1 g. diethylene glycol and 20.4 g. N-methyl-2-(2-hydroxyethoxy)acetamide was pumped by a syringe pump into the top of the reactor tube at a rate of 2.86 g./hr together with 60 ml/min. of hydrogen and 40 ml/min. of nitrogen with the catalyst bed temperature at 265°–273° C. The condensed effluent amounted to 91 percent of the weight of liquid feed mixture and was found by gas chromatographic analysis to contain 52 percent p-dioxanone and 47 percent N-methyldiglycolimide.

A sample of the imide (2.5 g.) was refluxed in 25 ml water with 18 ml Dowex 50W ion exchange resin, acid form, for 4 hours. Analysis of the resulting mixture showed that 91.2 percent of the imide had been converted to oxydiacetic acid while most of the remainder of the imide had been hydrolyzed to oxydiacetic acid monoamide.

Similarly, 2.5 g. of the imide in 25 ml of 0.8M HCl was refluxed for 2 hours to hydrolyze 76 percent of the starting imide to oxydiacetic acid and most of the remainder to the monoamide.

EXAMPLE 2

A feed mixture of diethylene gylcol and N-benzyl-2-(2-hydroxyethoxy)acetamide containing a small amount of p-dioxanone was prepared by adding 43.9 g. (0.41 g. mole) of benzylamine to a solution of 46 g. (0.45 g. mole) of p-dioxanone in 54 g. of diethylene glycol and heating the mixture on a water bath to complete the reaction after the initial exotherm was past. The resulting solution was pumped with a syringe pump at 5 ml/hr into the top of the reactor described in Example 1. Hydrogen was passed through the catalyst bed at 100 ml/min. with the liquid solution. the catalyst bed of 10 ml 20–40 mesh copper chromite (Girdler G-13 catalyst) had been reduced as in Example 1 and was maintained at about 280° C so that the amide dehydrogenation took place in the liquid phase.

The condensed reactor effluent was a slightly darker brown than the liquid feed. It was analyzed by vapor phase chromatography to confirm the presence of N-benzyldiglycolimide.

EXAMPLE 3

A U-tube reactor was made of a 15-inch length of half-inch 316 stainless steel pipe. A thermocouple well of quarter-inch stainless steel tubing extended through the 30 cc of usable catalyst bed space which was heated by immersion in a molten salt bath. The reactor was loaded with 30 ml of the catalyst used in Example 2 and this was reduced as before by a $H_2$-$N_2$ mixture at 200° C.

The feed mixture was prepared by adding 72.7 g. of isopropylamine to 300 g. of a solution of 46 weight percent p-dioxanone in diethylene glycol, using a flask equipped with both a water-cooled condenser and one cooled by solid carbon dioxide. After the initial reaction exotherm, the mixture was heated on a steam bath for 2 hours to complete the reaction. The feed mixture, which then consisted of a solution of N-isopropyl-2-(2-hydroxyethoxy)acetamide in diethylene glycol with a small amount of excess p-dioxanone, was cooled to room temperature and transferred to the feed reservoir.

The temperature of the salt bath was raised to 275° C and the feed mixture was pumped into the preheater section of the U-tube reactor at a rate of 15 ml per hour together with 600 ml/min. of hydrogen. As in the reactions in the foregoing examples, there was an initial large endotherm in the first part of the catalyst bed. The condensed reactor effluent was found by vapor phase chromatography to contain a substantial proportion of the expected product, N-isopropyldiglycolimide.

EXAMPLE 4

A mixture of equal parts by weight of N-methyldiethanolamine (NMDEA) and 2-(2-hydroxyethylmethylamino)-N-methylacetamide was prepared by adding methylamine to a solution of 4-methyl-2-morpholinone in NMDEA and heating until the reaction of the amine with the morpholinone was complete. Using the reactor and catalyst described in Example 1, 10 ml/hr of the above solution and 217 ml/min. of hydrogen was passed through the catalyst bed at 250° C. Gas chromatographic analysis of the reactor effluent showed that the expected N-methylimide of N-methyliminodiacetic acid (1,4-dimethyl-2,6-piperazinedione) had been formed in good yield. This compound is readily hydrolyzed to the Na salt of N-methyliminodiacetic acid when warmed in dilute aqueous NaOH.

The dehydrogenation of NMDEA to 4-methyl-2-morpholinone was found to proceed smoothly with high conversion and efficiency under the conditions employed above for the mixed feed.

EXAMPLE 5

A series of runs under various reaction conditions was made using the catalyst and reactor described in Example 3. A solution containing 63 percent by weight p-dioxanone and 37 percent diethylene glycol was pumped at the specified rate into an absorber where it was combined with methylamine in the proportions indicated. This mixture passed into the preheater section of the reactor where it was vaporized and combined with hydrogen before passing through the catalyst bed. The condensed effluent was analyzed by a gas-liquid chromatographic procedure for p-dioxanone, diethylene glycol, N-methyldiglycolimide (imide), and N-methyl-2-(2-hydroxyethoxy)acetamide (amide). Results are summarized in Table I.

TABLE I

| Temp. °C | LHSV[1] | R[2] | Hours | Mole Ratio, Dioxanone to Amine | Effluent Analysis, Wt. %[3] | | | |
|---|---|---|---|---|---|---|---|---|
| | | | | | Dioxanone | Glycol | Imide | Amide |
| 274 | 1.0 | 1300 | 3 | 1.15 | 35.8 | 3.8 | 48.0 | 4.0 |
| 272 | 1.0 | 1300 | 46 | 1.15 | 32.3 | 5.1 | 46.2 | 5.6 |
| 286 | 1.5 | 830 | 2 | 1.0 | 26.8 | 1.3 | 56.4 | 3.6 |
| 285 | 1.5 | 830 | 27 | 1.0 | 20.6 | 5.2 | 45.5 | 8.7 |
| 280 | 1.25 | 1973 | 3 | 1.0 | 34.1 | 1.5 | 58.8 | 5.5 |
| 277 | 1.25 | 1973 | 24 | 1.0 | 29.0 | 2.5 | 58.3 | 8.8 |
| 278 | 1.25 | 1973 | 76 | 1.0 | 24.0 | 3.3 | 52.4 | 17.7 |

[1]liquid space velocity, volumes per volume of catalyst per hour
[2]ratio ml/hr $H_2$ per ml/hr liquid feed
[3]weight balances averaged 92.4%, 87.1%, and 99.5% respectively for the three series of runs

EXAMPLE 6

Another run was made as described in Example 5 except that 97 percent p-dioxanone was the liquid feed. The absence of diethylene glycol from the liquid feed resulted in a comparatively rapid decline in catalyst activity as shown in Table II.

TABLE II

| Temp. °C | LHSV | R | Hours | Mole Ratio, Dioxanone to Amine | Effluent Analysis, Wt. % | | | |
|---|---|---|---|---|---|---|---|---|
| | | | | | Dioxanone | Glycol | Imide | Amide |
| 274 | 0.5 | 2500 | 4 | 1.11 | 7.9 | — | 80.8 | 2.0 |
| 274 | 0.5 | 2500 | 7 | 1.11 | 8.9 | — | 77.0 | 2.8 |
| 272 | 0.5 | 2500 | 24 | 1.11 | 14.3 | 1.2 | 37.6 | 17.1 |

The weight balance of condensed effluent declined from 91.2% at 4 hours to 71.7% at the end (based on the weight of feed).

EXAMPLE 7-9

A series of runs are made under the conditions of Example 5 using different copper chromite catalysts described in detail below. The effluent analyses in Table III show that catalysts Cu-1407 and G-22, while effective in the dehydrogenation, produce comparatively large amounts of the undesirable adduct of p-dioxanone and diethylene glycol. Catalyst G-22 also showed a rapid buildup of back pressure during the progress of the runs, indicating fouling of the catalyst bed. Catalyst G-13 showed generally good results with very small concentrations of the adduct byproduct consistent with results in Examples 1-6. Effluent samples were taken after several hours of running.

G-13 Girdler copper chromite, Cu/Cr1.62/1
G-22 Girdler copper chromite containing 12 percent BaO stabilizer, Cu/Cr1.2/1
Cu-1407 Harshaw copper chromite, Cu/Cr=0.83/1
Catalyst Cu-1407 was used in the form of ⅛ inch pellets, the others were crushed pellets.

TABLE III

| Catalyst | Temp. °C | LHSV | Effluent Analysis, Weight Percent | | | | | Percent Conversion[2] |
|---|---|---|---|---|---|---|---|---|
| | | | Glycol | Dioxanone | Imide | Amide | Adduct[1] | |
| Cu-1407 | 275 | 0.5 | 11.6 | 11.7 | 34.7 | 27.4 | 14.5 | 56.8 |
| " | 272 | 1.0 | 21.9 | 5.9 | 13.9 | 30.4 | 28.2 | 22.7 |
| " | 288 | 1.0 | 16.2 | 10.3 | 18.8 | 35.8 | 18.9 | 30.7 |
| G-22 | 274 | 0.5 | 13.4 | 25.5 | 38.3 | 10.2 | 12.6 | 80.0 |
| " | 271 | 1.0 | 20.9 | 16.8 | 28.6 | 12.6 | 21.1 | 59.8 |
| " | 290 | 1.0 | 14.1 | 16.1 | 40.8 | 12.7 | 16.3 | 85.3 |
| " | 270 | 1.5 | 29.4 | 4.3 | 16.8 | 22.5 | 27.0 | 35.1 |
| G-13 | 274 | 1.0 | 3.7 | 49.0 | 39.1 | 2.6 | 0.8 | 88.6 |
| " | 272 | 1.5 | 8.9 | 40.2 | 36.7 | 4.7 | 2.6 | 83.2 |

[1]adduct of p-dioxanone and diethylene glycol
[2]based on the available methylamine By methods described in the foregoing examples, other imides having R or R' substituents as indicated can be prepared and these imides, of course, are similarly hydrolyzable to the corresponding diacids. For example, octylamine is reacted with p-dioxanone to make N-octyl-2-(2-hydroxyethoxy)acetamide and this is dehydrogenated to make N-octyldiglycolimide and toluidine is reacted with p-dioxanone to produce N-tolyl-2-(2-hydroxyethoxy)acetamide which is dehydrogenated to make N-tolydiglycolimide. Similarly, N-phenyldiethanolamine is dehydrogenated to make 4-phenyl-2-morpholinone which is reacted with butylamine and the resulting amide dehydrogenated to produce 1-butyl-4-phenyl-2,6-piperazinedione.

All of these cyclic imides are readily hydrolyzed as previously described to make oxydiacetic acid and N-substituted iminodiacetic acid. These dicarboxylic acids are useful chelating agents, particularly for Ca and Mg ions in hard water. They are also useful chemical intermediates, for example, to make polyester plastics by reaction with a diol such as ethylene glycol, 1,4-butanediol, or the like.

I claim:
1. A process for making a compound having the formula

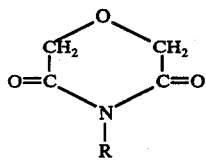

wherein R is a hydrocarbon group of 1–8 carbon atoms, which process comprises dehydrogenating by contacting a compound of the formula

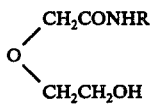

with a reduced copper dehydrogenation catalyst in the presence of hydrogen at a temperature of about 200°–300° C.

2. The process of claim 1 wherein the compound

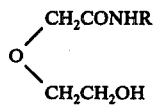

is contacted with the copper catalyst in the presence of excess hydrogen.

3. The process of claim 2 wherein the compound is contacted with the copper catalyst as a mixture of said compound with diethylene glycol.

4. The process of claim 1 wherein the catalyst is a reduced copper chromite catalyst.

* * * * *

UNITED STATES PATENT AND TRADEMARK OFFICE
CERTIFICATE OF CORRECTION

PATENT NO. : 4,082,748
DATED : April 4, 1978
INVENTOR(S) : George D. Shier

It is certified that error appears in the above-identified patent and that said Letters Patent are hereby corrected as shown below:

Column 3, line 63, delete the word "gylcol" and insert
-- glycol --.

Column 4, line 5, delete the word "the" (second occurrence) and substitute -- The --.

Column 5, delete the title "EXAMPLE 7-9" and insert
-- EXAMPLES 7-9 --.

Column 5, line 58, delete the word "are" and insert -- was --.

Column 6, line 43, delete the word "N-tolydiglycolimide" and insert -- N-tolyldiglycolimide --.

Signed and Sealed this

Twenty-second Day of August 1978

[SEAL]

Attest:

RUTH C. MASON
Attesting Officer

DONALD W. BANNER
Commissioner of Patents and Trademarks